United States Patent [19]

Babu et al.

[11] Patent Number: 5,506,279
[45] Date of Patent: Apr. 9, 1996

[54] ACRYLAMIDO FUNCTIONAL DISUBSTITUTED ACETYL ARYL KETONE PHOTOINITIATORS

[75] Inventors: Gaddam N. Babu, Woodbury, Minn.; Greggory S. Bennett, Hudson, Wis.; Kejian Chen, Woodbury, Minn.; Steven M. Heilmann, Afton, Minn.; Howell K. Smith, II, Grant Township, Minn.; Louis E. Winslow, Stillwater, Minn.

[73] Assignee: Minnesota Mining and Manufacturing Company, St. Paul, Minn.

[21] Appl. No.: 237,399

[22] Filed: May 3, 1994

Related U.S. Application Data

[63] Continuation-in-part of Ser. No. 136,576, Oct. 13, 1993, abandoned.

[51] Int. Cl.⁶ ........................................... C08F 2/46
[52] U.S. Cl. ................... 522/34; 522/35; 522/36; 522/904; 560/40; 560/221
[58] Field of Search ....................... 522/34, 35, 36, 522/904; 560/40, 221

[56] References Cited

U.S. PATENT DOCUMENTS

| | | | |
|---|---|---|---|
| 4,304,705 | 12/1981 | Heilmann et al. | 428/461 |
| 4,777,276 | 10/1988 | Rasmussen | 556/419 |
| 4,874,822 | 10/1989 | Rasmussen | 525/279 |
| 4,922,004 | 5/1990 | Kohler et al. | 560/221 |
| 5,274,167 | 12/1993 | Lange et al. | 560/40 |

FOREIGN PATENT DOCUMENTS

| | | |
|---|---|---|
| 0281941 | 9/1988 | European Pat. Off. |
| 235908 | 9/1990 | Japan. |
| 248482 | 10/1990 | Japan. |

OTHER PUBLICATIONS

Radcure '86, Conf. Proc., 10th, (Sep. 8–11, 1986) Baeumer et al., pp. 4–43 to 4–55.

*Primary Examiner*—Mark Chapman
*Attorney, Agent, or Firm*—Gary L. Griswold; Walter N. Kirn; Lorraine R. Sherman

[57] ABSTRACT

The invention provides novel acrylamide functional disubstituted acetyl aryl ketones and a process for their preparation in high yields uncontaminated by difunctional material. The invention further provides photocrosslinkable compositions comprising one or more ethylenically-unsaturated monomers and as photoinitiator the acrylamide functional disubstituted acetyl aryl ketone of the invention. The compositions are useful for the preparation of films and coatings, particularly pressure-sensitive adhesive coatings.

30 Claims, No Drawings

ACRYLAMIDO FUNCTIONAL DISUBSTITUTED ACETYL ARYL KETONE PHOTOINITIATORS

This is a continuation-in-part application of application Ser. No. 08/136,576, filed Oct. 13, 1993, now abandoned.

FIELD OF THE INVENTION

This invention relates to novel compounds useful as photoinitiators for the polymerization of free radically polymerizable ethylenically-unsaturated compounds. The invention further relates to photoinitiators that are copolymerizable with ethylenically-unsaturated compounds and to polymerizable compositions containing the photoinitiators. The invention also relates to a process for the production of the photoinitiators. In addition, the invention relates to pressure-sensitive adhesives and tape articles prepared using the photoinitiators of the invention.

BACKGROUND OF THE INVENTION

The use of photoinitiators to bring about the polymerization of free radically polymerizable compounds and compositions is well known and many photoinitiators are commercially available. The selection of a particular photoinitiator for use in a composition is generally made on the basis of the solubility, rate of reaction, activating wavelength, and intended use of the photoinitiator (e.g., use as protective coatings, viscoelastic products, and the like).

Until recently, photoinitiators have been radiation sensitive compounds that, on exposure to activating radiation of monomer compositions containing them, will in the absence of polyfunctional monomers in the composition induce polymerization of the monomers in a composition to essentially linear thermoplastic polymers. Included among these initiators are acyloin and derivatives thereof, e.g., benzoin, benzoin methyl ether, benzoin ethyl ether, benzoin isopropyl ether, benzoin isobutyl ether, and α-methylbenzoin, organic sulfides, e.g., diphenyl sulfide, diphenyl disulfide, decyl phenyl sulfide, and tetramethylthiuram monosulfide, S-acyl dithiocarbamates, e.g., S-benzoyl-N,N-dimethyldithiocarbamate, and α-substituted acetophenones, e.g. α,α-dimethyl-α-hydroxy acetophenone, α,α-diethoxy acetophenone. The initiator is generally used in amounts ranging from about 0.01 to 5.0% by weight of the total polymerizable composition.

Photosensitive compounds are known that when incorporated into photopolymerizable compositions bring about the crosslinking of the composition with attendant enhancement of the cohesive strength of the composition. Examples of these photoactive compounds include: sulfonyl halides, such as β-naphthalene sulfonyl chloride; halogenated aromatic compounds, such as α-chloromethylnaphthalene; and trichloromethyl-s-triazines, such as 2,4-bis(trichloromethyl)-6-(4-methoxystyryl)-s-triazine. These photosensitive compounds, although very effective for use in the polymerization and photocrosslinking of monomer containing compositions liberate hydrogen chloride as a by-product, following hydrogen abstraction by chlorine radicals which are responsible for initiating the polymerization and crosslinking. The corrosiveness of the liberated hydrogen chloride makes these photosensitive crosslinkers unsatisfactory for some purposes.

Photosensitive compounds that can bring about the crosslinking of monomer containing compositions without the liberation of hydrogen chloride are disclosed in European Patent Application No. 0 281 941. In this application, coreactive photoinitiators are disclosed that have the general formula:

$$RG—A—IN \qquad \text{I}$$

in which IN denotes a photoinitiator structure, A denotes a spacer group, and RG denotes a functional group. This extremely broad Formula I includes acryloyloxy functional photosensitive compounds and acrylamidoacyl functional photosensitive compounds such as

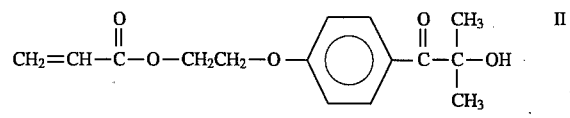

2-propenoic acid, 2-[4-(2-hydroxy-2-methylpropanoyl) phenoxy]ethyl ester II, also called 2-hydroxy-1-[4-(2-acryloyloxyethoxy)phenyl]-2-methyl-1-propanone) and

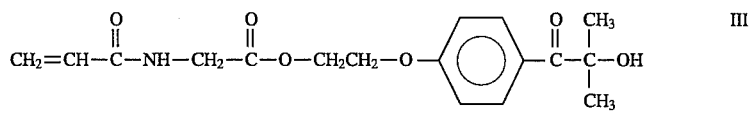

2-propenoylaminoethanoic acid, 2-[4-(2-hydroxy-2-methylpropanoyl)phenoxy]ethyl ester, III.

Acryloyloxy functional photosensitive compound II is also disclosed in RADCURE '86, Conf. Proc., 10th, 4/43–4/55 (Sep. 8–11, 1986); and its preparation in U.S. Pat. No. 4,922,004, among other patents in which it is taught that Compound II is prepared in a calculated 60% yield from 2-hydroxy-1-[4-(2-hydroxyethoxy)phenyl] -2-methyl-1-propanone (Irgacure™ 2959, Ciba-Geigy, Chicago, Ill.) by reaction with acryloyl chloride.

Acrylamidoacetyl functional photosensitive compounds such as Compound III are included in the EP application 281,941 formula RG-A-IN only by proper combination of groups from among the many groups disclosed as useful in the formula; the formula discloses for spacer group "A" only unsubstituted ($CH_2$) units.

Japanese KOKAI Patent HEI 2[1990]-248482 describes a photocurable pressure sensitive adhesive (PSA) suitable for screen printing enabling a high rate of production of printed circuit boards using as photoinitiator 1-acryloyloxy-2-[4-(4-chlorobenzoyl)benzoyloxy]ethane, a hydrogen abstracting photocrosslinker. Such a composition would yield an adhesive having a shear value of less than 100 minutes.

Japanese KOKAI Patent HEI 2[1990]-235908 discloses pressure sensitive adhesives by use of a composition of ethylenically-unsaturated cleavage type photopolymerization initiator such as 2-hydroxy-1-[4-(2-acryloyloxyethoxy)phenyl]-2-methyl-1-propanone [Formula II], a conventional photopolymerization initiator and a polyfunctional crosslinking agent such as hexanediol diacrylate. The PSA would have good shear primarily because of the conventional polyfunctional crosslinking agent. In the absence of such a conventional polyfunctional crosslinking agent the PSA would be expected to exhibit poor shear.

SUMMARY OF THE INVENTION

The present invention provides novel acrylamide functional disubstituted acetyl aryl ketones useful as photoinitiators which in polymerizable ethylenically unsaturated compositions, preferably acrylic compositions such as pressure-sensitive adhesive compositions, are more hydrolytically stable and have a higher rate of free radical homopropagation than that of corresponding acryloyloxy functional photoinitiators. In addition, use of these photoinitiators results in compositions possessing excellent shear strength whether polymerized in the presence or absence of conventional polyfunctional crosslinkers.

The invention also provides a process for the preparation of the acrylamide functional disubstituted acetyl aryl ketones in greater than 70% theoretical yield comprising the steps of (a) providing a hydroxyl, thiol, or primary amine functional aryl ketone and (b) reacting the hydroxyl, thiol, or primary amine functional aryl ketone with an alkenyl azlactone.

The invention further provides photocrosslinkable compositions comprising (a) one or more photopolymerizable ethylenically-unsaturated compounds, (b) an acrylamide functional disubstituted acetyl aryl ketone photoinitiator, and (c) optionally, a photoinitiator not having an ethylenically unsaturated functional group. These compositions provide "PSAs" with higher molecular weights between crosslinks than conventional crosslinked PSAs. The photocrosslinkable and photocrosslinked compositions provide pressure-sensitive adhesives which can be used in tape and laminate constructions.

The invention also provides pressure-sensitive adhesives and products prepared therefrom comprising the polymerization product of the acrylamide functional disubstituted acetyl aryl ketone photoinitiator, at least one acrylic acid ester of a monohydric alcohol having an average of 4 to 12 carbon atoms, and at least one ethylenically unsaturated monomer whose homopolymer has a glass transition temperature greater than 50° C.

In this application:

"acrylamido" and "acrylamide" are used interchangeably;

"alkyl" means the monovalent group remaining after removal of a hydrogen atom from a linear, cyclic, or branched chain hydrocarbon containing 1 to 20 carbon atoms;

"lower alkyl" or "lower alkoxy" means $C_1$ to $C_6$ alkyl or alkoxy;

"aryl" means the monovalent group remaining after removal of one hydrogen atom from an aromatic hydrocarbon having 6 to 12 carbon atoms and optionally up to 3 heteroatoms selected from S, N, and nonperoxidic O, and includes substituted aromatic compounds in which the substituents can be up to three groups selected from lower alkyl ($C_1$ to $C_6$) and lower alkoxy ($C_1$ to $C_6$) groups;

"acrylamido functional disubstituted acetyl aryl ketone compounds" mean any of 2-(N-acrylamido)-2,2-disubstituted acetoxy-functional aryl ketones, 2-(N-acrylamido)-2,2-disubstituted thiolacetoxy-functional aryl ketones, 2-(N-acrylamido)-2,2-disubstituted acetamido-functional aryl ketones;

"arenyl" means the monovalent residue remaining after the removal of a hydrogen atom from an aromatic hydrocarbon containing both alkyl and aryl groups;

"arylene" means the divalent group remaining after removal of two hydrogens from an aromatic hydrocarbon having 6 to 12 carbon atoms and optionally up to 3 heteroatoms selected from S, N, and nonperoxidic O, and includes substituted aromatic compounds in which the substituents can be up to three groups selected from lower alkyl and lower alkoxy groups;

"acryl" "acryloyl" "acryloyloxy" "acrylamido" and "acrylamidoacyl" are intended to include also the corresponding "methacryl" "methacryloyl" "methacryloyloxy" "methacrylamido" and "methacrylamidoacyl";

"disubstituted acetyl" means an acetyl group in which the carbon atom between the amide and carbonyl groups is substituted by two alkyl groups or by one alkyl group and one aryl group;

"group" means a chemical species that allows for substitution or which may be substituted by conventional substituents which do not interfere with the desired product, e.g., substituents can be alkoxy, phenyl, halo (F, Cl, Br, I), cyano, nitro, etc.

The novel ketones contain ethylenically unsaturated substituents such that they participate directly in the polymerization reaction and their residues become incorporated into the polymer structure, which then retains the photoinitiating properties.

No art of which Applicants are aware disclose acrylamidoacetyl functional photoinitiators, which in acrylic pressure-sensitive adhesive compositions have a higher rate of free radical propogation than that of the corresponding acryloyloxy functional photoinitiators.

DETAILED DESCRIPTION

The novel acrylamide functional disubstituted acetyl aryl ketones of the invention have the general formula IV

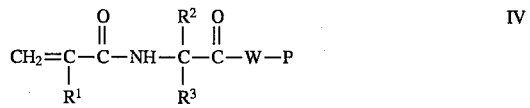

wherein $R^1$ is hydrogen or methyl;

$R^2$ and $R^3$ are independently an alkyl group of 1 to 14 carbon atoms, a cycloalkyl group of 3 to 14 carbon atoms, an aryl group of 5 to 12 ring atoms, an arenyl group having 6 to 16 carbon atoms and up to 3 heteroatoms selected from S, N, and nonperoxidic O, or $R^2$ and $R^3$ taken together with the carbon atom to which they are joined form a carbocyclic ring of 4 to 12 ring atoms;

W is -X- or a divalent connecting group joining the carbonyl group of the acrylamidoacetyl functional group to a photosensitive aryl ketone group, P; W is preferably selected from the class of connecting groups consisting of

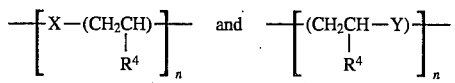

in which n is a number having a value of one to four, $R^4$ is hydrogen or methyl group, X is -O-, -S-, or -NH-, and Y is

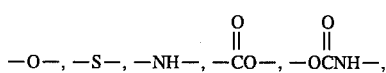

-continued

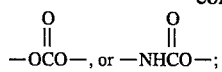

P can be a radiation sensitive aryl ketone group capable of Norrish Type I cleavage. (Basic photochemistry of aryl ketones is discussed in a text by J. G. Calvert and J. N. Pitts, Jr., "Photochemistry" John Wiley & Sons, Inc., New York (1966) pp 377–389.) Preferably P is selected from radiation sensitive groups having the formula:

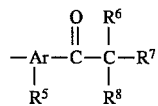

in which

Ar is an arylene group having 6 to 12 carbon atoms that can be substituted by a lower alkyl group having one to six carbon atoms, Ar preferably is selected from phenylene, naphthalenylene, and biphenylene; and $R^5$ is selected from the group consisting of hydrogen, $C_1$ to $C_{12}$ alkyl groups, $C_1$ to $C_{12}$ alkoxy groups, and phenyl groups;

$R^6$, $R^7$, and $R^8$ independently are selected from the group consisting of hydroxyl, $C_1$ to $C_{12}$ alkyl groups, $C_1$ to $C_{12}$ alkoxy groups, di($C_1$ to $C_{12}$) amino groups, and aryl groups, provided that at least one of $R^6$, $R^7$ and $R^8$ is selected from the group consisting of hydroxyl, $C_1$ to $C_{12}$ alkoxy groups, or $C_1$ to $C_{12}$ amino groups, or that any two of $R^6$, $R^7$, and $R^8$ together can be an alkylene group, $-(C_p H_{2p})-$, or an alkylene-dioxy group, $-O-(C_p H_{2p})-O-$, in which p is an integer having a value of two or three, that together with the carbon atoms to which they are attached to form a 5- or 6-membered ring, or any two of $R^6$, $R^7$, and $R^8$ taken together with the carbon atom to which they are attached can form a carbonyl group

provided that the remaining $R^6$, $R^7$, or $R^8$ is selected from the group consisting of hydroxyl, $C_1$ to $C_{12}$ alkoxy groups, $C_1$ to $C_{12}$ amino groups, and aryl groups.

Examples of acrylamido functional disubstituted acetyl aryl ketone photoinitiators of Formula IV according to the invention include:

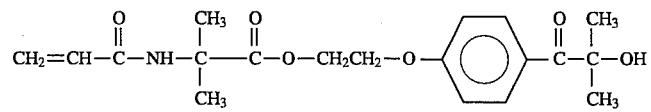

1.

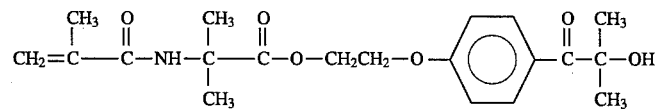

2.

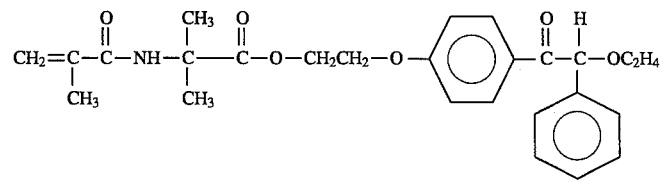

3.

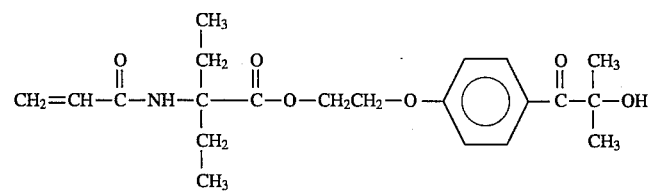

4.

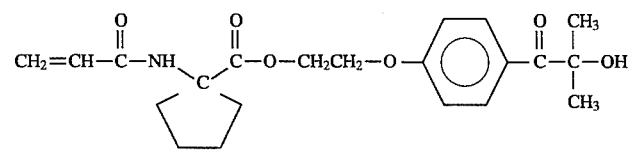

5.

-continued

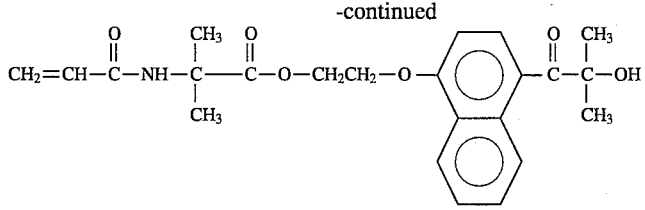
6.

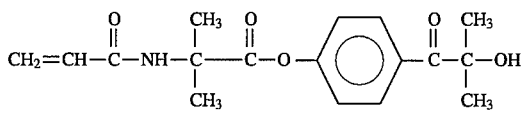
7.

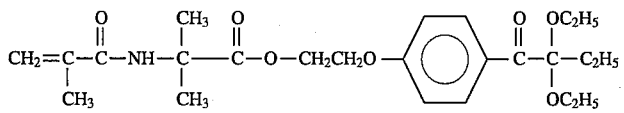
8.

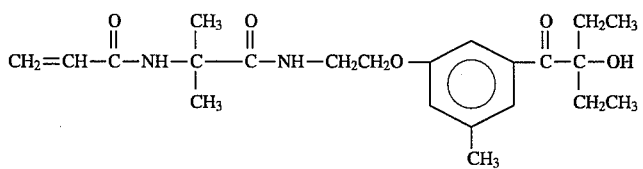
9.

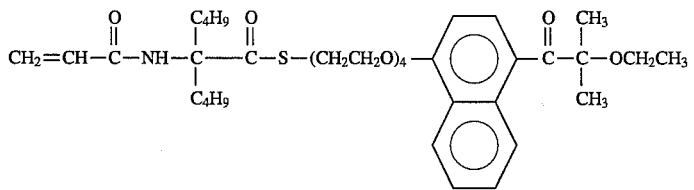
10.

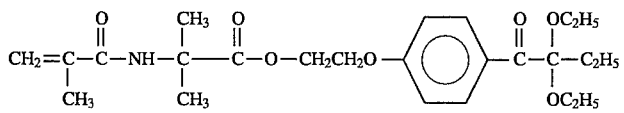
11.

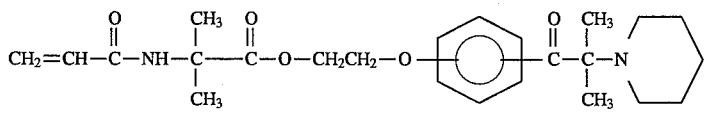
12.

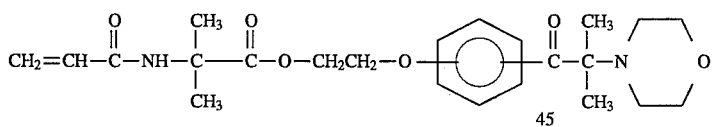
13.

The acrylamido functional disubstituted acetyl aryl ketone photoinitiators of the invention preferably are prepared by reaction of a hydroxy, thiol, or amine functional aryl photoinitiator having the formula H-W-P, wherein W and P are as previously defined, with an equivalent amount of a 4,4-disubstituted alkenyl azlactone in accordance with the reaction scheme:

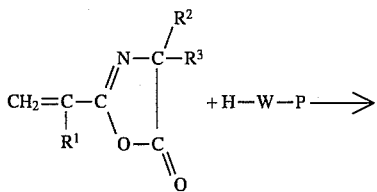

Alkenyl azlactone (Formula V)   Hydroxyl, thiol, or amine functional aryl ketone (Formula VI)

-continued

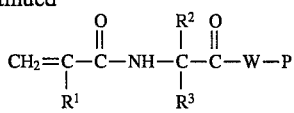

Arylamido functional disubstituted acetyl aryl ketone photoinitiator (Formula VII)

wherein $R^1$, $R^2$, $R^3$, W and P are the same as defined above.

One class of the acrylamide functional disubstituted acetyl aryl ketones is prepared by the reaction of an azlactone with a hydroxy, thiol or amine functional aryl ketone according to the reaction scheme:

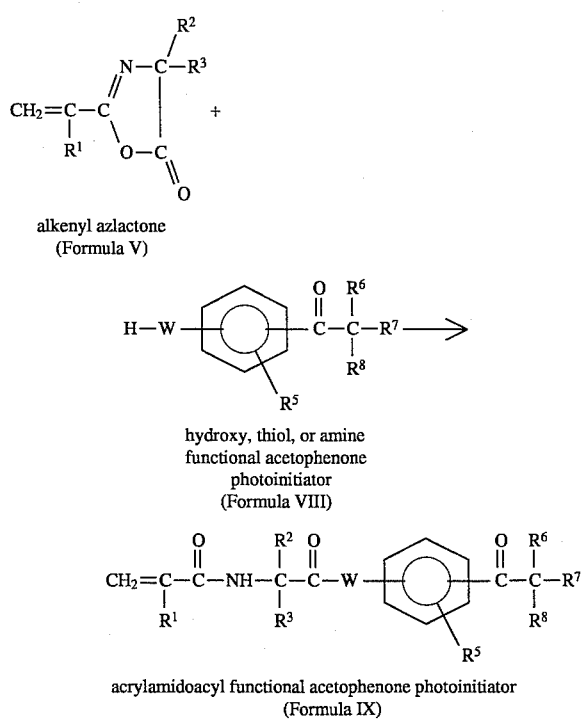

alkenyl azlactone
(Formula V)

hydroxy, thiol, or amine
functional acetophenone
photoinitiator
(Formula VIII)

acrylamidoacyl functional acetophenone photoinitiator
(Formula IX)

wherein $R^1$, $R^2$, $R^3$, $R^5$, $R^6$, $R^7$, $R^8$, and W are the same as defined above.

The reaction of the alkenyl azlactone with the hydroxy, thiol, or amine functional aryl ketone is preferably carried out in the presence of an effective amount of a catalyst selected from:

(a) bicyclic amidines such as, for example, 1,5-diazabicyclo[4.3.0]non-5-ene (DBN), 1,8-diazabicyclo[5.4.0]undec-7-ene (DBU), and 1,5,7-triazabicyclo[4.4.0]dec-5-ene (TBD). Additional information relating to these compounds is given in U.S. Pat. No. 4,874,822, which is incorporated herein by reference for that purpose, and (b) compounds comprising trivalent phosphorous, such as trimethylphosphine, triethylphosphine, tributylphosphine, trioctylphosphine, tris(dimethylamino)phosphine, dimethylphenylphosphine, diphenylmethylphosphine, 1,2-bis(di-n-propyl-phosphino)ethane, 1,3-bis(diphenylphosphino)propane, diethylmethoxyphosphine, and triphenylphosphine.

The amount of the initiator utilized in the instant process may vary from about 0.05 mole percent (based on alkenyl azlactone) to about 10 mole percent or more. In most cases, however, 0.5 to 5 mole percent are sufficient to provide a reasonable reaction rate.

Alkenyl azlactones of Formula V of use in the preparation of the photoinitiators of the invention are well known in the art, and include: 4,4-dimethyl-2-ethenyl-2-oxazolin-5-one (also known as 2-vinyl-4,4-dimethylazlactone), 4,4-dimethyl-2-isopropenyl-2-oxazolin-5-one, 2-ethenyl-4-methyl-4-phenyl-2-oxazolin-5-one, 2-ethenyl-4,4-pentamethylene-2-oxazolin-5-one, 4,4-diphenyl-2-isopropenyl-2-oxazolin-5-one, and 2-ethenyl -4-ethyl-4-methyl-2-oxazolin-5-one. Others are disclosed in assignee's U.S. Pat. No. 4,777,276, and in U.S. Pat. No. 4,304,705, which are incorporated herein by reference.

The hydroxy, thiol, and amine functional aryl ketones of Formula VI from which the acrylamidoacetyl functional ketones of the invention can be prepared by methods known to those in the art such as are described in Krepski, et al., Tetrahedron Letters 24,(38) pp 4075–4078 (1983). Some of the aryl photoinitiators of Formula VI are available commercially, such as 2-hydroxy-1-[4 -(2-hydroxyethoxy)phenyl]-2-methyl-1propanone (available as Irgacure™ 2959 from Ciba-Geigy, Chicago, Ill.).

The preferred conditions for carrying out the process of the invention are to mix the reactants and catalyst in the absence of solvent and to allow the reaction to proceed at room temperature (about 22° C). These conditions, however, may be modified in certain instances as is clear to one skilled in the art. For example, reaction temperatures below (in the case of exothermic reactions) or above room temperature (for very slow reactions or in the case of solid reactants) may be advantageous. In general, reaction temperatures from about 0° C. to about 100° C. or so may be utilized to carry out the process of the instant invention. Also, in certain cases nonreactive solvents or diluents may be utilized to facilitate or mediate the reaction. By "nonreactive" is meant that the solvents do not contain functional groups which can react with either the azlactone, the hydroxy, thiol, or amine functional molecule, or the catalyst under the conditions utilized. Suitable nonreactive organic solvents include, for example, ethyl acetate, toluene, xylene, acetone, methyl ethyl ketone, acetonitrile, tetrahydrofuran, hexane, heptane, dimethylformamide, dimethylacetamide, and the like, or combinations thereof. In many instances, it may also be advantageous to add an effective amount of an antioxidant or free radical inhibitor (e.g. 0.00005 to 5.0 weight percent based on the combined weight of azlactone and hydroxy, thiol, or amine functional photoinitiator) such as a hindered phenol, to the reaction mixture or the final acrylamide functional product.

While in most instances it may be preferable to carry out the process of the invention so as to have a 1:1 stoichiometric balance of alkenyl azlactone to hydroxy, thiol, or amine functional groups, thus converting all of these groups into acrylamide groups, it is also considered to be within the scope of the invention to utilize more or less (e.g. from 50 to 150 mole %) than an equivalent amount of azlactone based upon the hydroxy, thiol, or amine equivalent weight.

As should be obvious to one skilled in the art, the reaction time required to convert the hydroxy, thiol, or amine functional compounds of Formula VI to the acrylamido functional disubstituted acetyl aryl ketones of Formula IV will vary widely. Reaction times will depend upon several factors, including the nature of the functional group of Formula VI, the substituents of the azlactone, the type of catalyst used, the amount of catalyst, the concentration of reactants and the temperature of the reaction. Progress of the reaction of the alkenyl azlactone with the hydroxy, thiol or amine functional molecule is readily monitored by infrared spectroscopy by following the disappearance of the azlactone carbonyl stretching absorption near 1800 cm$^{-1}$ (about 5.5 micrometers). The absence of competing side reactions and estimation of acrylamide equivalent weights may be determined conveniently by $^1$H-NMR analysis.

The photopolymerizable compositions of the invention comprise one or more photopolymerizable ethylenically unsaturated monomers and the acrylamido functional disubstituted acetyl aryl ketone photoinitiators. The compositions are useful for the preparation of films and coatings for use on various substrates including paper, plastics, wood, metal, glass and ceramics. Suitable photopolymerizable monomers for use in the compositions are selected from any of the free radically polymerizable ethylenically-unsaturated monomers, examples of which include one or more of the vinyl aromatic monomers such as styrene, α-methylstyrene, 2- and 4-vinyl pyridine, and the like; a,β-unsaturated carboxylic acids and their derivatives such as acrylic acid, methacrylic acid, itaconic acid, maleic acid, fumaric acid, crotonic acid, methyl methacrylate, butyl methacrylate, 2-ethylhexyl methacrylate, ethyl acrylate, butyl acrylate, iso-octyl acrylate, octadecyl acrylate, cyclohexyl acrylate, tetrahydrofurfuryl methacrylate, phenyl acrylate, phenethyl acrylate, benzyl methacrylate, β-cyanoethyl acrylate, maleic anhydride, diethyl itaconate, acrylamide, methacrylonitrile, N-butylacrylamide, and the like; vinyl esters of carboxylic acids such as vinyl acetate, vinyl 2-ethylhexanoate, and the like; vinyl halides such as vinyl chloride, vinylidene chloride, and the like; vinyl ethers such as ethyl vinyl ether, butyl vinyl ether, 2-ethylhexyl vinyl ether, and the like; N-vinyl compounds such as N-vinylpyrrolidone, N-vinylcarbazole, and the like; vinyl ketones such as methyl vinyl ketone and the like; and vinyl aldehydes such as acrolein, methacrolein, and the like; hydroxy functional vinyl mononers such as 2-hydroxyethyl acrylate, 2-hydroxyethyl methacrylate, 2-hydroxyethyl acrylamide, 2-hydroxyethyl maleimide, 4-hydroxybutyl vinyl ether, glycerol monoacrylate or methacrylate, and diethyleneglycol monomethacrylate.

Polyunsaturated monomers can also be used to provide additional cohesive strength, if desired, in the acrylamide functional disubstituted acetyl aryl photoinitiator-containing compositions of the invention such as polyfunctional acrylates, for example, ethylene glycol diacrylate, 1,6-hexanediol diacrylate, propoxylated bisphenol A diacrylate and dimethacrylate, trimethylolpropane triacrylate and pentaerythritol triacrylate. Also useful in the compositions are unsaturated oligomers and polymers including, for example, acrylated polyesters, polyethers, and silicone polymers. A preferred polyunsaturated monomer is hexanediol diacrylate. Copolymerizable polyunsaturated monomers can be present in the polymerizable composition in the range of 0 to 5.0 pbw (parts by weight), preferably 0.01 to 5.0 pbw, more preferably 0.01 to 2.0 pbw, and most preferably 0.01 to 0.5 pbw.

In preferred crosslinkable compositions of the invention, the use of as little as 0.05 part by weight of polyunsaturated monomer will reduce the amount of acrylamide functional disubstituted acetyl aryl photoinitiator required to obtain high shear values to no more than about 0.05 part by weight.

The photopolymerizable compositions of the invention can be stabilized by adding known thermal inhibitors and antioxidants, such as, for example, hydroquinone or hydroquinone derivatives, pyrogallol, thiophenols, nitro compounds, or β-napthols, in the customary amounts without significantly impairing the initiating action of the photoinitiators according to the invention. The main purpose of such additions is to prevent premature polymerization during the preparation of the systems.

Depending on its intended use, the composition of the invention can contain, for example, plasticizers, viscosifiers, flatting agents, bacteriocides, fillers, lubricants, surfactants, pigments, dyes, and other agents. The amounts of these materials used is selected to provide the characteristics desired in the final cured composition. The amounts to be added vary with the intended use.

The acrylamide functional disubstituted acetyl aryl ketone photoinitiator and ethylenically-unsaturated monomers of the invention can be homopolymerized or they can be copolymerized to linear products that can be crosslinked by exposure to actinic radiation. By the term "actinic radiation" is meant radiation having wavelengths in the 200 to 600 nm range, preferably 280 to 450 nm, and more preferably 300–450 nm. Suitable sources include sunlight, carbon arcs, mercury vapor arcs, black light lamps, fluorescent lamps, argon and xenon glow lamps, electronic flash units and flood lamps. Particularly useful intensities include those in the range of 0.1 to 150 mW/cm$^2$, preferably in the range of 0.5 to 100 mW/cm$^2$ and more preferably in the range of 0.5 to 50 mW/cm$^2$. Depending on the concentration of photoinitiator, the particular acrylamide functional disubstituted acetyl aryl ketone photoinitiator and the depth of the composition, exposures necessary to polymerize (which term includes polymerize and crosslink) the composition range from about 1 second or less to about 10 minutes or longer.

In a first process, ethylenically unsaturated monomers and the novel photoinitiator(s) of the invention and preferably a conventional photoinitiator (such as those disclosed in the Background of the Invention, preferably Irgacure 2959 (Ciba-Geigy)) can be partially polymerized to provide a syrup having a coatable viscosity. Such a syrup comprises a linear polymer having pendent photoinitiator groups. This can be accomplished by thermal techniques leading to linear polymer or by exposure to actinic radiation leading to branched polymer.

Such polymers can be used as polymeric photoinitiators and can have the general formula:

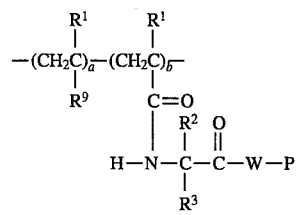

in which $R^1$, $R^2$, $R^3$, W and P are the same as defined above; $R^9$ is one or more organic groups as determined by the identity of the ethylenically-unsaturated monomers in the polymerizable composition, preferably $R^9$ is selected from alkoxy groups and alkoxy carbonyl groups having 1 to 20 carbon atoms, aryl, and arenyl groups (where these groups are as previously defined), and a and b are each numbers having a value sufficient to provide to the linear polymer a number average molecular weight of from about 1000 to 5,000,000, the mole ratio, b/(a+b), having a value from about 0.0001 to 0.5.

In a second process, it is possible to polymerize the monomer composition containing an ethylenically unsaturated monomer and the novel photoinitiator of the invention to a linear polymer having pendent photoinitiator groups. This can be accomplished by including in the composition a conventional source of free radicals that contains no copolymerizable group and is activated by heat or actinic radiation of a wavelength different from that of the acrylamide functional disubstituted acetyl aryl ketone photoinitiator.

A third process for the preparation of the polymeric photoinitiator of formula X comprises the steps of polymerizing an alkenyl azlactone of formula V with a copolymerizable ethylenically unsaturated monomer, and reacting the resulting copolymer with a hydroxy, thiol, or amino group-substituted photoinitiator of formula VI to provide the polymeric photoinitiator of formula X.

Such a polymer of formula X containing pendent photoinitiator groups, preferably having a Tg in the range of −70° to 150° C. can be added either to an acrylic syrup (partially polymerized material prepared from one or more acrylic monomers) or to at least one ethylenically unsaturated monomer to provide a composition polymerizable to a crosslinkable pressure-sensitive adhesive having desirable high performance properties.

The preferred photocrosslinkable composition of the invention comprises per 100 parts by weight (pbw):

(1) 60 to 99.95 pbw of one or more acrylic acid esters of monohydric aliphatic alcohols having an average of 4 to 12 carbon atoms;

(2) 0 to 39.95 pbw of ethylenically-unsaturated monomers whose homopolymer has a glass transition temperature (Tg) greater than 50° C., and (3) 0.01 to 10.0 pbw of acrylamide functional disubstituted acetyl aryl ketone photoinitiator, (4) 0 to 5.0 pbw of a polyfunctional acrylate, and (5) 0 to 5.0 pbw of a thermal or actinic radiation activated source of free radicals, the source being unsubstituted by ethylenic unsaturation.

A pressure-sensitive adhesive (PSA) is generally a component of a pressure-sensitive tape which in its most simple configuration is comprised of the adhesive and a backing, and the overall construction is tacky and adherent at the use temperature (typically room temperature) and adheres to a variety of substrates using only moderate (typically fingertip) pressure to form the bond. In this fashion, pressure-sensitive tapes constitute a complete, self-contained bonding system.

In the present invention, normally tacky and pressure-sensitive adhesive tapes represent a very versatile family of products, performing such diverse functions as insulating, mounting, sealing, mending, holding, masking, labeling, binding, joining, laminating, protecting, and reinforcing. The tapes can be single or double coated (i.e., PSA on both surfaces of a substrate) and can be applied to a substrate.

When coated on a flexible backing, the photocrosslinkable or photocrosslinked compositions can provide pressure-sensitive adhesive tapes having desirable hydrolytic stability. A layer of a conventional release material can be included in the tape construction which can then be provided as a roll of pressure-sensitive adhesive tape. In addition, a pressure-sensitive adhesive of the invention can be included between two substrates to provide a laminated construction. At least one of the substrates can be nonadhering or can be releasing to the PSA.

TEST METHODS

The following tests may be used to evaluate the adhesive tapes of the invention.

Static Shear Value

The adhesive films as described in the examples were cut into strips 1.27 cm in width and adhered by its adhesive to a flat, rigid stainless steel plate with exactly 1.27 cm length of tape in contact with the plate. Before testing, a 1000 g weight at 25° C. was placed over the bonded area for 15 minutes. Then the plate with the adhered tape was placed either at room temperature (RT) or in an air-circulating oven which had been preheated to 70° C., and after 15 minutes a 500 g or 1000 g weight was hung from the free end of the tape, with the panel tilted 2° from the vertical to insure against any peeling forces. The time (in minutes) at which the weight fell was the "Static Shear RT (1000 g) or 70° C. (500 g)". The test was discontinued at 10,000 minutes if there was no failure. In the Tables, this was designated as 10,000+ minutes.

Peel Adhesion

Peel adhesion was measured as in ASTM D-3330-78 except that the test tapes were 1.27 cm in width and were tested immediately after being adhered to a glass or stainless steel surface. Results were reported in Newtons per/decimeter (N/dm).

Percent Gel Test [ASTM D-3616-82]

The gel test was performed as described in U.S. Pat. No. 5,112,882, col. 10, line 18 to col. 11, line 2, which is incorporated herein by reference.

The objects and advantages of the invention are further illustrated by the following examples, but the particular materials and amounts thereof recited in these examples, as well as other conditions and details, should not be construed to unduly limit this invention. Unless stated otherwise, all parts are parts by weight and all temperatures are degree centigrade.

EXAMPLES

Example 1

Preparation of the acrylamidoacetyl photoinitiator:

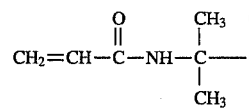 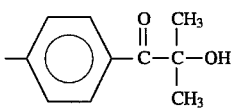

Compound No. 1

Into a 200 ml round bottom flask fitted with a magnetic stirrer were placed 22.4 g (0.1 mole) of

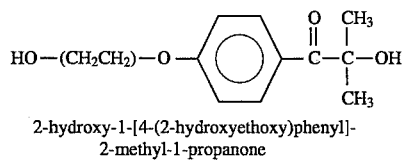

2-hydroxy-1-[4-(2-hydroxyethoxy)phenyl]-
2-methyl-1-propanone (available as Irgacure™ 2959 from Ciba-Geigy), 14.2 g (0.102 mole) of 2-vinyl-4,4-dimethyl-2-oxazolin-5-one (VDM) (available from SNPE Inc., Princeton, N.J. 08540), and 50 ml of amyl acetate. While stirring the mixture, 0.76 g of 1,8-diazabicyclo[5.4.0]undec-7-ene (DBU) (available from Aldrich Chemical Co., Milwaukee, Wis.) was added. Heat was evolved as the reaction components went into solution, and after complete solution was obtained, stirring was discontinued. The mixture was allowed to cool to room temperature and the solid that had formed was collected by filtration. After drying the recovered solid in a vacuum oven at about 40° C., there was obtained 32.6 g of reaction product (89.8% of theory). The material had a melting point of 84.5°–85.5° C. (uncorrected). Elemental Analysis, Infrared Spectral Analysis, and $^1$H and $^{13}$C Nuclear Magnetic Resonance confirmed that the material was the title compound.

Example 2

Preparation of the methacrylamidoacetyl photoinitiator

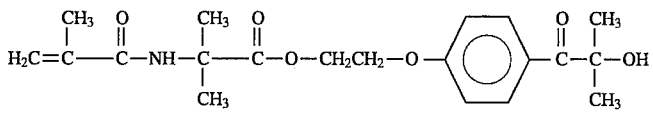

Compound No. 2

The procedure of example 1 was utilized except that 2-isopropenyl-4,4-dimethyl-2-oxazolin-5-one (IDM; prepared as described by Taylor, et al., J. Polym. Sci. Polym, Lett. Ed., 1971, 9, 187) was utilized instead of VDM. The reaction was run on a 0.5 mole scale. After drying in a vacuum oven at about 40° C. there was obtained 141.6 g of reaction product (75% of theory). The material had a melting point of 69°–71° C. (uncorrected). $^1$H and $^{13}$C Nuclear Magnetic Resonance confirmed that the material was the title compound.

Example 3

Preparation of the acrylamidoacetyl photoinitiator:

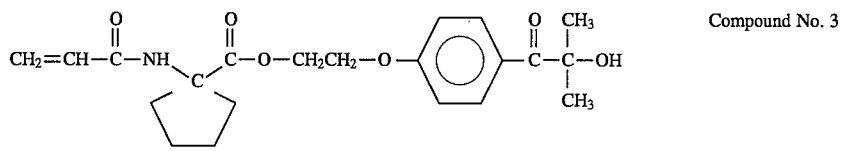

Compound No. 3

Step 1. Preparation of 2-ethenyl-4,4-pentamethylene-2-oxazolin-5-one.

Into a 500 ml round bottom flask equipped with a reflux condenser and a magnetic stirrer were placed 9.15 g (0.05 mole) 1-acrylamidocyclopentane carboxylic acid (prepared by the method described by Heilmann et al., Synthetic Communications 17(7), 843–862(1987), 10.32 g (0.05 mole) of the dehydrating agent, N,N'-dicyclohexylcarbodiimide (available from Aldrich Chemical Co.) and 150 ml methylene chloride and the mixture was stirred for 18 hours. The resulting slurry was filtered to remove N,N'-dicyclohexylurea formed during the reaction, and the methylene chloride was removed under reduced pressure at room temperature. The azlactone obtained was used in Step 2 without further purification.

Step 2. Condensation of Product from Step 1 and Irgacure™ 2959

The procedure of Example 1 was repeated using a) the azlactone of Step 1, b) 11.2g (0.05 mole) Irgacure™ 2959, c) 40 ml amyl acetate, and d) 5 drops of DBU.

There was obtained 17.5 g (90.0% of theory) of the acrylamidoacetyl photoinitiator of the title. It had an uncorrected melting point of 119°–121° C. Infrared, Elemental, and $^1$H and $^{13}$C Nuclear Magnetic Resonance (NMR) spectral analyses confirmed that the material was the title material, Compound No. 3.

Comparative Example 1

Preparation of:

mole) Irgacure 2959, 9.90 g (0.048 mole) N,N-dicyclohexylcarbodiimide, 150 ml methylene chloride, and 0.57 g (0.005 mole) trifluoroacetic acid. The mixture was stirred at room temperature (about 22° C.) for 75 hours. The solid that had collected was removed by filtration and the filtrate was concentrated under reduced pressure to an oil. After standing at room temperature for 7 days the oil solidified. The solid was recrystallized from ethyl acetate and dried in a vacuum oven at 60° C. There was obtained 9.0 g (56.0% of theory based on Irgacure 2959) showing an uncorrected melting point of 93°–94° C. After a sample of this material was recrystallized from ethyl acetate/pentane, its uncorrected melting point was 94.5°–95.5° C. Elemental analysis, $^1$H and $^{13}$C NMR spectra confirmed that the material was that of the title compound.

Example 4

Preparation of isooctyl acrylate/acrylic acid, and acrylamidoacetyl photoinitiator (Compound 1) terpolymer (Polymer I):

Nine grams of (90/10 parts by weight) of isooctyl acrylate and acrylic acid, 1 gram of Compound 1, 100 grams of ethyl acetate, 0.1 gram of carbon tetrabromide (a chain transfer agent) and 0.1 gram of benzoyl peroxide were charged into a bottle. The bottle was purged with nitrogen for 10 minutes. The bottle was capped, placed in a water bath at 60° C. and agitated for approximately 20–24 hours. The viscosity of the solution increased and the infrared spectrum of the polymer showed the disappearance of the vinyl monomer. The solvent was removed on a rotary evaporator. The mixture was precipitated in methanol and dried under vacuum to constant weight.

Example 5

Preparation of isobornyl acrylate/acrylic acid and acryamidoacetyl photoinitiator (Compound 1) terpolymer (Polymer II)

Nine grams of (90/10 parts by weight) of isobornyl acrylate and acrylic acid, 1 gram of Compound 1, 100 grams of ethyl acetate, 0.1 part of carbon tetrabromide (a chain transfer agent) and 0.1 gram of benzoyl peroxide were charged into a bottle. The bottle was purged with nitrogen for 10 minutes, capped, placed in a water bath at 60° C. and agitated for approximately 20–24 hours. The viscosity of the solution increased and the infrared spectrum of the polymer

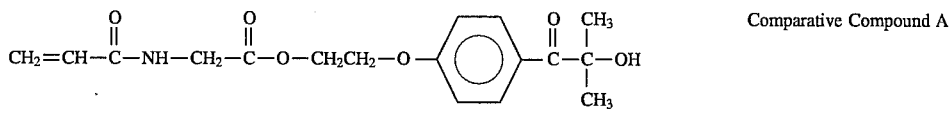

Comparative Compound A

Into a 500 ml flask fitted with a magnetic stirrer and reflux condenser were placed 6.46g (0.05 mole) N-acryloylglycine (prepared according to the procedure of Kulkarni and Morawetz, J. Polymer Sci., 54, 491 (1961)), 10.75 g (0.048 showed the disappearance of the vinyl monomer. The solvent was removed on a rotary evaporator. The mixture was precipitated in methanol and dried under vacuum to constant weight.

Example 6
Preparation of copolymer of isooctyl acrylate-acrylamido functional initiator (Polymer III)

92.5 g of isooctyl acrylate and 7.5 g of vinyldimethylazlactone, 100 g of ethyl acetate, 0.1 g of carbon tetrabromide (a chain transfer agent) and 0.1 g of benzoyl peroxide were charged to a bottle. The bottle was purged with nitrogen for 10 minutes. The bottle was capped, placed in a water bath at 60° C. and agitated for approximately 20–24 hours. The viscosity of the solution increased and the infrared spectrum of the polymer showed the disappearance of the carbon-carbon double bonds. The reaction bottle was charged with 11.97 grams of Irgacure™ 2959 and 0.7 g of 1,8-diazabicyclo[5.4.0] -undec-7-ene. The reaction mixture was heated at 60° C. under nitrogen. The progress of the reaction was followed by infrared spectroscopy. At the end of the reaction, the solvent was removed on a rotary evaporator. The mixture was stirred in methanol and the precipitated polymer having pendent photoinitiator groups was dried under vacuum to constant weight.

Example 7
Preparation of isobornyl acrylateacrylamido functional initiator (Polymer IV)

92.5 g of isobornyl acrylate and 7.5 g of vinyldimethylazlactone, 100 g of ethyl acetate, 0.1 g of carbon tetrabromide (a chain transfer agent) and 0.1 g of benzoyl peroxide were charged to a bottle. The bottle was purged with nitrogen for 10 minutes. The bottle was capped, placed in a water bath at 60° C. and agitated for approximately 20–24 hours. The viscosity of the solution increased and the infrared spectrum of the polymer showed the disappearance of the carbon-carbon double bonds. The reaction bottle was charged with 11.97 grams of Irgacure™ 2959 and 0.7 g of 1,8-diazabicyclo[5.4.0]undec-7-ene. The reaction mixture was heated at 60° C. under nitrogen. the progress of the reaction was followed by infrared spectroscopy. At the end of the reaction, the solvent was removed on a rotary evaporator. The mixture was stirred in methanol and the precipitated polymer having pendent photoinitiator groups was dried under vacuum to constant weight.

Example 8
Preparation of pressure-sensitive adhesives
A monomer mixture was prepared to contain:

90 pbw isooctyl acrylate (IOA)

10 pbw acrylic acid (AA)

0.04 pbw 2,2-dimethoxy-2-phenylacetophenone (KB-1™) (available from Sartomer)

To portions of the monomer mixture was added 0.3 to 1.0% by weight of Compound No. 1, dimethyl substituted acrylamidoacetyl functional photoinitiator of Example 1 or 0.3 to 0.7% by weight of Comparative Compound A, the dihydroacrylamidoacyl functional photoinitiator of the Comparative Example. Each portion was partially (5 to 10%) photopolymerized in bulk in an inert (nitrogen) atmosphere using a bank of 40-watt fluorescent blacklights to provide coatable syrups of a viscosity (Brookfield) of about 1500 cps.

Each coating syrup was knife-coated onto 40 μm poly(ethylene terephthalate)film (PET) at a thickness of 40μm. The coating was exposed to a bank of blacklight bulbs (about 300–400 nm). The coating was exposed to an intensity of about 2.2 mW/cm$^2$ for about 2.0 minutes. Each coating received an irradiated dose of about 250 mJ/cm$^2$. Properties of the various pressure-sensitive tapes are recorded in Table I.

TABLE I

| Photo-initiator | Wt % | Peel adhesion[a] N/dm | Shear holding 25° C.[b] min. |
| --- | --- | --- | --- |
| Compound No. 1 | 0.3 | 80 | 5997 |
|  | 0.7 | 66 | 6876 |
|  | 1.0 | 66 | 10,000+ |
| Comparative A | 0.3 | 67 | 384 |
|  | 0.4 | 66 | 2509 |
|  | 0.7 | 66 | 4303 |

[a]Peel adhesion was measured from glass at 180° C. also using a 230 cm/minute peeling rate.
[b]Shear holding values were determined employing (½" × ½") 1.27 cm × 1.27 cm areas of adhesive adhered to stainless steel plates and a suspending load of 1000 g at 25° C.

It can be seen from the data in Table I that pressure-sensitive adhesives prepared using the photoinitiator of the invention, Compound No. 1, have peel adhesions in the same range as the peel adhesions of the adhesives prepared with dihydroacrylamidoacetyl photoinitiator, Comparative Compound A, and that the shear holding strengths of adhesives prepared using Compound No. 1 are greater than 10,000 minutes at 25° C. while the shear holding strengths of adhesives prepared using Comparative Compound A are less than 4500 minutes at 25°.

Example 9
A series of pressure-sensitive adhesive tapes were made by first partially polymerizing a mixture of, by weight, 90 pbw of isooctyl acrylate 10 pbw of acrylic acid 1.30 pbw of Compound No. 1.

The partial photopolymerization was accomplished in an inert (nitrogen) atmosphere using a bank of 40-watt fluorescent blacklights to provide a coatable syrup. The mixture was knife coated onto 40 μm poly(ethylene terephthalate) (PET) film to different thicknesses. The coating was exposed to a bank of blacklight bulbs. The coating was subjected to different irradiated doses. The reaction conditions and properties of various pressure-sensitive tapes are recorded in Table II.

TABLE II

| S. No. | Oxygen (ppm) | Energy (mJ/cm$^2$) | Thickness (μm) | Peel adh. (N/dm) | Shear (min.) | Gel (%) | Volatiles (%)[b] | I[a] mW/cm$^2$ | Time sec. |
| --- | --- | --- | --- | --- | --- | --- | --- | --- | --- |
| 1. | 96 | 298 | 45 | 80 | 10,000+ | 86 | 0.77 | 2.65 | 111 |
| 2. | 114 | 298 | 90 | 104 | 10,000+ | 86 | 1.15 | 2.65 | 111 |
| 3. | 119 | 279 | 47 | 82 | 10,000+ | 83 | 0.62 | 2.65 | 104 |
| 4. | 111 | 279 | 88 | 104 | 10,000+ | 83 | 1.22 | 2.65 | 104 |
| 5. | 113 | 279 | 120 | 130 | 10,000+ | 87 | 1.01 | 2.65 | 104 |
| 6. | 138 | 265 | 47 | 82 | 10,000+ | 83 | 0.92 | 2.65 | 99 |

TABLE II-continued

| S. No. | Oxygen (ppm) | Energy (mJ/cm$^2$) | Thickness (μm) | Peel adh. (N/dm) | Shear (min.) | Gel (%) | Volatiles (%)[b] | I[a] mW/cm$^2$ | Time sec. |
|---|---|---|---|---|---|---|---|---|---|
| 7. | 210 | 251 | 90 | 101 | 10,000+ | 88 | 1.14 | 2.65 | 93 |
| 8. | 114 | 237 | 48 | 84 | 10,000+ | 77 | 0.85 | 2.65 | 89 |
| 9. | 114 | 237 | 89 | 104 | 10,000+ | 88 | 1.34 | 2.65 | 89 |

Shear values were the average of three determinations measured at room temperature on 1.27 cm × 1.27 cm with 1 kg load at 25° C.
[a]I = intensity
[b]percent volatiles was gravimetrically determined after drying 3 hours at 120° C.

The data in Table II show that increase in thickness of the adhesives gave increased peel adhesions. All adhesives of Table II gave 10,000+ shear values independent of oxygen concentration.

Example 10

Pressure-sensitive adhesive prepared using both the photoinitiator of the invention and a polyfunctional acrylate.

A monomer mixture was prepared to contain 90 pbw isooctyl acrylate (IOA)

10 pbw acrylic acid (AA)

0.04 pbw KB-1.

To portions of the monomer mixture, as shown in Table III, was added 0 to 0.5 pbw of Compound No. 1. Each portion was partially polymerized to a coating syrup as described in Example 8. To each syrup 0.16 pbw KB-1 and 0 to 0.3 pbw of hexanediol diacrylate (HDDA) were added, as shown in Table III and each syrup was coated and cured by irradiation as follows:

All of the PSAs were cured on solvent free silicone paper release liner in a nitrogen-rich environment (250 ppm oxygen). 125 μm thick (5 mil) PSAs were cured with ultraviolet irradiation using 355 mJ/cm$^2$ of energy applied over 150 sec. Three average intensities for all samples of Table III were utilized (in order given): 1.0 mW/cm$^2$ for 50 sec., 2.1 mW/cm$^2$ for 95 sec., and 36 mW/cm$^2$ for 5 sec. Peel strength values were determined from stainless steel after it had been washed once with acetone and three times with a 50/50 isopropanol/water mixture. All peel strengths were determined using a 90° peel mode at 30.5 cm/minute. 1.27 cm wide samples with 125 μm thick (5 mil) anodized aluminum backings were used for all of the testing. The static shear strength values were measured from stainless steel substrates cleaned once with acetone and three times with a 50/50 isopropanol/water mixture. 2.54 cm×1.27 cm samples were prepared and a 1000 g load was used at room temperature and a 500 g load was used at 70° C. The time to bond failure was recorded. 125 μm thick (5 mil) anodized aluminum backings were used for all of the static shear samples. The percent volatiles were gravimetrically determined after drying for three hours at 120° C.

TABLE III

| Sample No. | Compd. No. 1 phr | HDDA phr | R.T. Shear min | 70° Shear min | 72 hr. Peel N/dm | Volatiles % |
|---|---|---|---|---|---|---|
| 1 | 0.1 | 0 | 10,000+ | 712 | 149 | 0.88 |
| 2 | 0.2 | 0 | 10,000+ | 10,000+ | 187 | 0.84 |
| 3 | 0.3 | 0 | 10,000+ | 10,000+ | 175 | 0.80 |
| 4 | 0.5 | 0 | 10,000+ | 10,000+ | 152 | 0.69 |
| 5 | 0.8 | 0 | 10,000+ | 10,000+ | 152 | 0.80 |
| 6 | 1.1 | 0 | 5,329 | 10,000+ | 181 | 0.83 |
| 7 | 0 | 0.02 | 10,000+ | 1,444 | 167 | 0.84 |
| 8 | 0 | 0.05 | 7,676 | 97 | 168 | 0.85 |
| 9 | 0 | 0.10 | 10,000+ | 126 | 169 | 0.83 |
| 10 | 0 | 0.15 | 10,000+ | 432 | 171 | 0.97 |
| 11 | 0 | 0.20 | 10,000+ | 156 | 184 | 0.95 |
| 12 | 0 | 0.25 | 10,000+ | 353 | 169 | 0.93 |
| 13 | 0 | 0.30 | 10,000+ | 765 | 160 | 0.86 |
| 14 | 0.01 | 0.02 | 8986 | 40 | 189 | 1.17 |
| 15 | 0.01 | 0.05 | 10,000+ | 144 | 206 | 1.15 |
| 16 | 0.01 | 0.10 | 10,000+ | 107 | 183 | 1.14 |
| 17 | 0.05 | 0.02 | 10,000+ | 380 | 167 | 1.08 |
| 18 | 0.05 | 0.05 | 10,000+ | 10,000+ | 194 | 1.13 |
| 19 | 0.05 | 0.10 | 10,000+ | 10,000+ | 199 | 1.04 |
| 20 | 0.10 | 0.02 | 10,000+ | 10,000+ | 200 | 0.87 |
| 21 | 0.10 | 0.05 | 10,000+ | 10,000+ | 159 | 0.88 |
| 22 | 0.10 | 0.10 | 10,000+ | 10,000+ | 166 | 0.74 |
| 23 | 0.20 | 0.02 | 10,000+ | 10,000+ | 210 | 0.79 |
| 24 | 0.20 | 0.05 | 10,000+ | 10,000+ | 152 | 0.75 |
| 25 | 0.20 | 0.10 | 10,000+ | 10,000+ | 160 | 0.76 |
| 26 | 0.50 | 0.02 | 10,000+ | 10,000+ | 161 | 0.71 |
| 27 | 0.50 | 0.05 | 10,000+ | 10,000+ | 178 | 0.74 |
| 28 | 0.50 | 0.10 | 10,000+ | 10,000+ | 148 | 0.77 |

The data of Table III show that compositions containing 0.02 to 0.30 HDDA (Samples 7–13) and no Compound No. 1 did not provide adhesives having 70° shear values above 1,444 minutes. The data of Table III do show that without HDDA, pressure-sensitive adhesives having 70° shear values of 10,000 minutes or more were not obtained with compositions containing 0.1 pbw or less of Compound No. 1 (Sample 1), however, with as little as 0.05 pbw of HDDA, compositions containing only 0.05 pbw of Compound No. 1 (Sample 18) gave an adhesive that had a 70° shear value of greater than 10,000 minutes. The adhesive of Sample 18 also had an excellent 72 hour peel value.

Example 11

A series of pressure-sensitive adhesive tapes were made by first partially polymerizing (according to the method of Example 8) a mixture of, by weight, 90 pbw of isooctyl acrylate 10 pbw of acrylic acid 0.04 pbw of 2,2-dimethoxy-2-phenylacetophenone (KB-1) (available from Sartomer) into a syrup.

Five grams of polymeric photoinitiator (Polymer I of Example 4 or Polymer II of Example 5) were added to each syrup and thoroughly mixed. The mixture was knife coated onto 40 μm poly(ethylene terephthalate) (PET) film at a thickness of 50 μm. The coating was, exposed to a bank of blacklight bulbs. Each coating received an irradiated dose of 250 mJ/cm$^2$, 2.4 mW/cm$^2$ for 104 seconds at an oxygen level of 193 ppm. The properties of various pressure-sensitive tapes are recorded in Table IV. Peel adhesion and shear holding values were measured as described in Example 8.

TABLE IV

| Polymeric photoinitiator | Wt % | Peel adhesion N/dm | Shear holding 25° C. | 70° C. |
|---|---|---|---|---|
| Polymer I | 5 | 68 | 10,000+ | 4890 |
| Polymer II | 5 | 58 | 10,000+ | 6810 |

The data of Table IV show that the addition of polymeric photoinitiators to partially polymerized acrylic syrups, followed by photochemically curing, provided pressure-sensitive adhesives having high performance properties.

Example. 12

Preparation of pressure-sensitive adhesives

A series of pressure-sensitive adhesive tapes was made by partially photopolymerizing a mixture of:

90 pbw isooctyl acrylate (IOA)

10 pbw acrylic acid (AA)

0.04 pbw 2,2-dimethoxy-2-phenylacetophenone

The partial photopolymerization was accomplished in an inert (nitrogen) atmosphere using a bank of 40-watt fluorescent black lights to provide a coatable syrup of a viscosity of about 1500 cps. A polymeric photoinitiator (polymer III of Example 6 or polymer IV of Example 7) was added to each syrup. Each mixture was coated at a thickness of 50 μm using a conventional knife coater onto biaxially-oriented polyethylene terephthalate film. The coated film was cured using the procedure of Example 11.

TABLE V

| Polymer | Parts by wt (g) | Oxygen in the chamber (ppm) | Peel adhesion N/dm | Shear values (min) |
|---|---|---|---|---|
| III | 2 | 195 | 74 | 1207 |
| III | 5 | 197 | 68 | 4400 |
| III | 10 | 202 | 69 | 6808 |
| IV | 2 | 207 | 70 | 2005 |
| IV | 5 | 194 | 72 | 6452 |
| IV | 10 | 199 | 69 | 8426 |

Each of the tapes had a peel adhesion in the range of 68 to 74 N/dm (measured from glass at 180°) and a peeling rate of 230 cm/min) and a 25° C. shear value of up to 8426 minutes.

Example 13

This example teaches the use of a methacrylamidoacetyl photoinitiator (Compound No. 2 of Example 2) in combination with a conventional photoinitiator (KB-1) and with a diacrylate additive (HDDA). Each of the following trials was prepared using partially polymerized syrups described in Example 10; additional KB-1 photoinitiator (0.12 wt. %) was then dissolved in each syrup. Coating and polymerizations to high conversions, i.e., greater than 98%, were also conducted as described in Example 10, and two irradiation conditions were utilized: Blacklight alone (in Trials 1–3; 250 mJ/cm$^2$ using an intensity of 2.4 mW/cm$^2$ for 147 seconds at an oxygen level of 200 ppm) and Blacklight followed by exposure to a medium pressure mercury lamp (in Trials 4–6; 70 mJ/cm$^2$ using an intensity of 16.9 mW/cm$^2$ for 8 seconds). The shear holding data recorded in Table VI below was obtained using 2.54 cm×1.27 cm (1.0"×0.5") adhesive areas and a 500 gram load at 70° C.; the values serve as a means of differentiating the effectiveness of Compound 2 in the presence and absence of diacrylate additives.

TABLE VI

| Trial No. | Compound No. 2 | HDDA | Blacklight Alone Shear Time (minutes) | Blacklight + Mercury Lamp Shear Times (minutes) | Peel Adhesion (N/dm) |
|---|---|---|---|---|---|
| 1 | 0.40 | — | 142 | 10,000+ | 158 |
| 2 | 0.80 | — | 7594 | 10,000+ | 144 |
| 3 | 1.20 | — | 10,000+ | 51 p.o.* | 139 |
| 4 | 0.05 | 0.10 | 17 | 434 | 157 |
| 5 | 0.10 | 0.10 | 27 | 10,000+ | 148 |
| 6 | 0.20 | 0.10 | 33 | 10,000+ | 157 |

*p.o. = pop-off failure

The data of trials 1–3 show that a concentration of about 1.20% Compound No. 2 is required for high performance shear holding capability, while the data of trials 4–6 show that the concentration of Compound No. 2 can be substantially reduced, i.e., to as little as 0.10%, when HDDA and post-Blacklight exposure to high intensity are utilized.

Example 14

This example teaches that a high performance pressure sensitive adhesive with low percentage volatiles can result from use of Compound No. 2 of Example 2 and high intensity exposure only.

The following trials were conducted by adding 1.3 weight percent of Compound No. 2 to the monomer solution of Example 8 and exposing the solutions to Blacklight until a coatable viscosity was achieved. Resulting syrups were knife-coated onto polyester, and the coated syrups were covered with a polyester cover sheet (50 micrometers in thickness) prior to exposure to the high intensity light from a medium pressure Hg lamp.

TABLE VIII

| Trial | Total Exposure (mJ) | % Volatiles | Shear Time (minutes) | Peel Adhesion (N/dm) | I(a) mW/cm$^2$ | Time sec. |
|---|---|---|---|---|---|---|
| 1 | 408 | 11.6 | — | — | 16.9 | 24 |
| 2 | 816 | 1.2 | 10,000+ | 108 | 16.9 | 48 |
| 3 | 1224 | 1.1 | 10,000+ | 105 | 16.9 | 72 |
| 4 | 1632 | 1.0 | 10,000+ | 107 | 16.9 | 96 |

(a)I = intensity

Trial 1 produced an unacceptable pressure sensitive tape because of an excessive level of percent volatiles in the form of unpolymerized monomers. When the amount of high intensity radiation was increased, however, in trials 2–4 very acceptable percent volatiles and tape performances were observed.

Various modifications and alterations of this invention will become apparent to those skilled in the art without departing from the scope and spirit of this invention, and it should be understood that this invention is not to be unduly limited to the illustrative embodiments set forth herein.

We claim:

1. The acrylamide functional disubstituted acetyl aryl ketone compound having the formula:

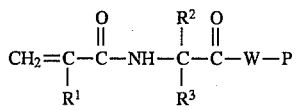

wherein

R¹ is hydrogen or methyl;

R² and R³ independently are an alkyl group of 1 to 14 carbon atoms, a cycioalkyl group of 3 to 14 carbon atoms, an aryl group of 5 to 12 ring atoms, an arenyl group having 6 to 16 carbon atoms, the aryl and arenyl groups up to 3 heteroatoms selected from S, N, and nonperoxidic O, or R² and R³ taken together with the carbon atom to which they are joined form a carbocyclic ring of 4 to 12 ring atoms;

W is -O-, -S-, or -NH- or a divalent connecting group joining the carbonyl group of the acrylamidoacetyl functional group to the photosensitive group, P; and P is a radiation sensitive aryl ketone group capable of Norrish Type I cleavage, said compound being a photoinitiator.

2. The acrylamide functional disubstituted acetyl aryl ketone according to claim 1 wherein W is selected from the class of connecting groups consisting of

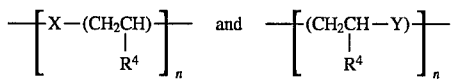

in which n is a number having a value of one to four, R⁴ is hydrogen or methyl group, X is -O-, -S-, or -NH-, and Y is selected from the group consisting of

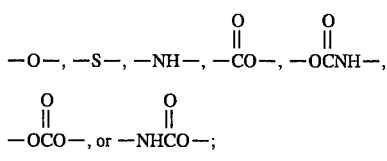

3. The acrylamide functional disubstituted acetyl aryl ketone according to claim 1 wherein the radiation sensitive group P has the formula:

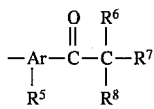

in which

Ar is an arylene group having 6 to 12 carbon atoms that can be substituted by a lower alkyl group having one to six carbon atoms; and R⁵ is selected from the group consisting of hydrogen, C₁ to C₁₂ alkyl groups, C₁ to C₁₂ alkoxy groups, and phenyl groups;

each R⁶, R⁷, and R⁸ independently are selected from the group consisting of hydroxyl, C₁ to C₁₂ alkyl groups, C₁ to C₁₂ alkoxy groups, di(C₁ to C₁₂) amino groups, and phenyl groups, provided that at least one of R⁶, R⁷ and R⁸ is selected from the group consisting of hydroxyl, C₁ to C₁₂ alkoxy groups, or C₁ to C₁₂ amino groups, or that any two of R⁶, R⁷, R⁸ together is an alkylene group, -(C$_p$H$_{2p}$)-, or an alkylene-dioxy group, -O-(C$_p$H$_{2p}$)-O-, in which p is an integer having a value of two or three, that together with the carbon atoms to which they are attached form a 5- or 6- membered ring, or any two of R⁶, R⁷, and R⁸ taken together with the carbon atom to which they are attached form a carbonyl group,

provided that the remaining R⁶, R⁷, or R⁸ is selected from the group consisting of hydroxyl, C₁ to C₁₂ alkoxy groups, C₁ to C₂ amino groups, and aryl groups.

4. The acrylamide functional disubstituted acetyl aryl ketone of claim 3 wherein Ar is selected from the group consisting of phenylene, naphthylenylene, and biphenylene.

5. The acrylamide functional disubstituted acetyl aryl ketone according to claim 1 having at least one of the formulae:

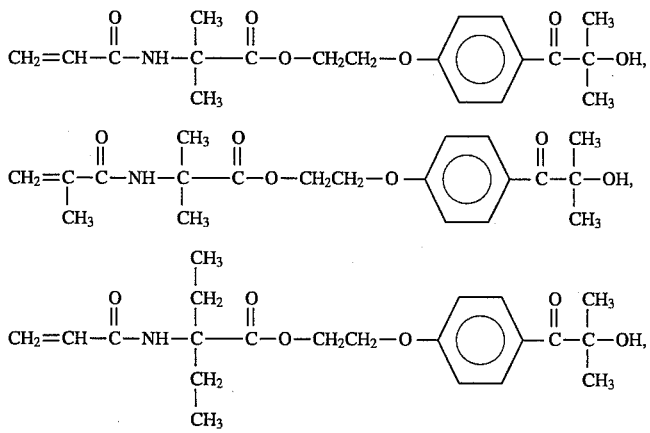

or

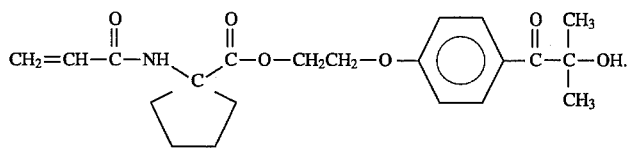

6. A photopolymerizable composition comprising one or more ethylenically-unsaturated monomers and an acrylamide functional disubstituted acetyl aryl ketone photoinitiator according to claim 1.

7. A composition photopolymerizable to a pressure-sensitive adhesive comprising per 100 parts by weight (pbw) of
  (1) 60 to 99.95 pbw of one or more acrylic acid esters of monohydric aliphatic alcohols, said alcohols having an average of 4 to 12 carbon atoms;
  (2) 0 to 39.95 pbW Of ethylenically-unsaturated monomers whose homopolymer has a glass transition temperature (Tg) greater than 50° C., and
  (3) 0.01 to 10.0 pbw of acrylamide functional disubstituted acetyl aryl ketone photoinitiator as defined in claim 2,
  (4) 0 to 5.0 pbw of a polyfunctional acrylate monomer, and
  (5) 0 to 5.0 pbw of a thermal or actinic radiation activated source of free radicals, the source being free of ethylenic unsaturation.

8. The composition according to claim 7 wherein said polyfunctional acrylate is hexanediol diacrylate.

9. The composition according to claim 7 wherein said copolymerizable polyunsaturated monomer is present in an amount in the range of 0.01 to 5.0 pbw.

10. The composition according to claim 7 wherein said acrylamide functional disubstituted acetyl aryl photoinitiator is present in an amount in the range of 0.01 to 2.0 weight percent.

11. The polymerized composition according to claim 7.

12. The composition according to claim 11 which has been polymerized using actinic radiation having intensities in the range of 0.1 to 150 mW/cm².

13. A substrate bearing a layer of the polymerized composition according to claim 11.

14. A substrate bearing a layer of the photopolymerizable adhesive composition of claim 7.

15. A process for preparing an acrylamide functional disubstituted acetyl aryl ketone comprising the steps of
  (a) providing an admixture of 100 mole percent of a hydroxyl, thiol, or amine functional aryl ketone with from 50 to 150 mole percent of one or more disubstituted alkenyl azlactones;
  (b) maintaining the admixture at 0° C. to 100° C. for a sufficient time to convert the hydroxyl, thiol, or amine functional aryl ketone to an acrylamide functional disubstituted acetyl aryl ketone as defined in claim 2;
  (c) optionally, isolating the resulting acrylamide functional disubstituted acetyl aryl ketone which is a photoinitiator.

16. The process of claim 15 wherein the hydroxy, thiol, or amine functional aryl ketone has the formula H-W-P, wherein W and P are as defined above and the alkenyl azlactone has the formula

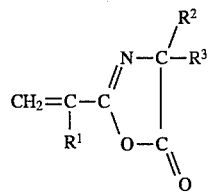

wherein R¹, R², and R³ are defined above.

17. The process of claim 15, wherein P is

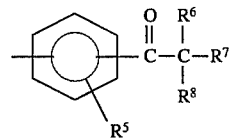

wherein R⁶, R⁷, and R⁸ are defined above, and
wherein R⁵ is a lower alkyl group of 1 to 6 carbon atoms.

18. The process according to claim 15 further comprising the step of polymerizing said acrylamide functional disubstituted acetyl aryl ketone with at least one ethylenically unsaturated monomer to provide a crosslinked polymer.

19. A pressure sensitive adhesive tape comprising a flexible backing and on at least one surface thereof a layer of the photopolymerized composition according to claim 11.

20. The pressure sensitive adhesive tape according to claim 19 further comprising a layer of a release coating.

21. A roll of tape comprising the pressure sensitive adhesive tape according to claim 20.

22. A laminated article comprising the pressure-sensitive adhesive according to claim 11 applied between two substrates.

23. The laminated article according to claim 22 wherein at least one substrate is nonadherent to the pressure sensitive adhesive.

24. A polymeric photoinitiator comprising units having the formula

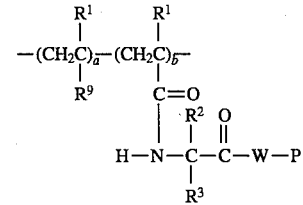

in which R¹, R², R³, W, and P are the same as defined above; R⁹ is one or more groups as determined by the identity of the ethylenically-unsaturated monomers in the polymerizable composition; and a and b are each numbers having a value sufficient to provide to the linear polymer a number average molecular weight of from about 1000 to 5,000,000, the mole ratio, b/(a+b), having a value from about 0.0001 to 0.5.

25. A photopolymerizable composition comprising one or more ethylenically unsaturated monomers and the polymeric photoinitiator having units according to claim 24.

26. The photopolymerizable composition according to claim 25 which is a coatable syrup.

27. A pressure sensitive adhesive composition comprising the polymerized composition according to claim 25.

28. A pressure sensitive adhesive tape comprising a flexible backing and on at least one surface thereof the pressure sensitive adhesive composition according to claim 27.

29. A laminated article comprising the pressure-sensitive adhesive tape according to claim 27 applied to a substrate.

30. A process for preparing the polymeric photoinitiator according to claim 24 comprising the steps of:
 a) polymerizing an alkenyl azlactone with a copolymerizable ethylenically unsaturated monomer, and
 b) reacting the resulting copolymer with a hydroxy, thiol, or amino group-substituted photoinitiator to yield said polymeric photoinitiator.

* * * * *